(12) United States Patent
Biederman et al.

(10) Patent No.: US 11,850,070 B2
(45) Date of Patent: *Dec. 26, 2023

(54) ADHESIVE LAYER APPLICATION DEVICE FOR WEARABLE HARDWARE

(71) Applicant: Verily Life Sciences LLC, South San Francisco, CA (US)

(72) Inventors: William Biederman, San Francisco, CA (US); Sean Frick, San Francisco, CA (US); Roxana Heitz, Mountain View, CA (US)

(73) Assignee: VERILY LIFE SCIENCES LLC, South San Francisco, CA (US)

(*) Notice: Subject to any disclaimer, the term of this patent is extended or adjusted under 35 U.S.C. 154(b) by 173 days.

This patent is subject to a terminal disclaimer.

(21) Appl. No.: 17/201,630

(22) Filed: Mar. 15, 2021

(65) Prior Publication Data
US 2021/0196200 A1 Jul. 1, 2021

Related U.S. Application Data

(63) Continuation of application No. 16/410,910, filed on May 13, 2019, now Pat. No. 10,945,668.

(Continued)

(51) Int. Cl.
*A61B 5/00* (2006.01)
*A61B 5/01* (2006.01)
(Continued)

(52) U.S. Cl.
CPC .............. *A61B 5/6833* (2013.01); *A61B 5/01* (2013.01); *A61B 2560/0412* (2013.01);
(Continued)

(58) Field of Classification Search
CPC . A61B 5/6832; A61B 5/6833; A61B 5/04087; A61B 5/68335; A61B 5/01; A61B 2560/0412; A61B 2562/164; A61B 2560/0209; A61B 2560/0219; A61B 2560/164; A61B 5/0533; Y10T 156/1744; Y10T 156/17; Y10T 156/1763;
(Continued)

(56) References Cited

U.S. PATENT DOCUMENTS

| 2009/0145788 A1* | 6/2009 | Doshi | B26F 1/02 |
| | | | 206/370 |
| 2009/0155594 A1* | 6/2009 | Evans | A61B 5/259 |
| | | | 428/411.1 |

(Continued)

*Primary Examiner* — Philip C Tucker
*Assistant Examiner* — Brian R Slawski
(74) *Attorney, Agent, or Firm* — Haynes and Boone, LLP

(57) ABSTRACT

An adhesive layer applicator for a body-mountable device is disclosed. The applicator includes a housing defining a first opening through which a chamber is accessible, and a plurality of adhesive layers and a plurality of adhesive liners alternately stacked on a floor that is movable within the chamber. The size and shape of the opening corresponds to the size and shape of the body-mountable device. The housing is configured to receive at least a portion of the body-mountable device through the opening. A second opening is formed in each adhesive layer in the plurality of adhesive layers and a gel is accommodated within the second openings.

18 Claims, 6 Drawing Sheets

Related U.S. Application Data

(60) Provisional application No. 62/671,863, filed on May 15, 2018.

(51) Int. Cl.
| | | |
|---|---|---|
| *B65D 83/08* | (2006.01) | |
| *B29C 65/78* | (2006.01) | |
| *B32B 38/10* | (2006.01) | |
| *B29C 65/76* | (2006.01) | |
| *B29C 65/48* | (2006.01) | |
| *B32B 37/12* | (2006.01) | |
| *B29C 65/00* | (2006.01) | |
| *B32B 7/06* | (2019.01) | |
| *B29C 65/72* | (2006.01) | |

(52) U.S. Cl.
CPC ..... *A61B 2562/164* (2013.01); *B29C 65/4825* (2013.01); *B29C 65/72* (2013.01); *B29C 65/76* (2013.01); *B29C 65/7814* (2013.01); *B29C 65/7858* (2013.01); *B29C 66/47* (2013.01); *B32B 7/06* (2013.01); *B32B 37/1284* (2013.01); *B32B 38/10* (2013.01); *B65D 83/0817* (2013.01)

(58) Field of Classification Search
CPC ......... Y10T 428/14; B32B 38/10; B32B 7/06; B32B 7/12; B32B 37/12; B32B 37/1269; B32B 37/1284; B65D 83/08; B65D 83/0805; B65D 83/0811; B65D 83/0817; B65D 83/0888; B29C 63/00; B29C 63/004; B29C 63/013; B29C 65/00; B29C 65/48; B29C 65/4825; B29C 65/486; B29C 65/50; B29C 65/5057; B29C 65/5092; B29C 65/72; B29C 65/76; B29C 65/7802; B29C 65/7805; B29C 65/7814; B29C 65/7858; B29C 66/47; B29C 66/472

USPC ....... 156/60, 64, 94, 98, 152, 230, 235, 239, 156/247, 249, 281, 289, 293, 303.1, 701, 156/714, 719, 349, 389, 423, 535, 536, 156/538, 539, 540, 556, 564, 565, 573; 600/386, 391, 392; 206/363, 370; 428/40.1, 41.8, 41.9

See application file for complete search history.

(56) References Cited

U.S. PATENT DOCUMENTS

| | | | | |
|---|---|---|---|---|
| 2015/0129437 | A1* | 5/2015 | Clamp | B65D 81/22 53/445 |
| 2015/0351689 | A1* | 12/2015 | Adams | A61B 5/6833 600/300 |
| 2016/0120450 | A1* | 5/2016 | Sakurai | A61B 5/14552 600/310 |
| 2016/0317092 | A1* | 11/2016 | Lee | A61B 5/6833 |
| 2016/0361015 | A1* | 12/2016 | Wang | B32B 27/26 |

\* cited by examiner

ADHESIVE LAYER APPLICATION DEVICE FOR WEARABLE HARDWARE

CROSS-REFERENCE TO RELATED APPLICATIONS

This application is a continuation of U.S. application Ser. No. 16/410,910, filed May 13, 2019, which claims the benefit of the filing date of, and priority to, U.S. Application No. 62/671,863, filed May 15, 2018, the entire disclosures of which are hereby incorporated herein by reference.

BACKGROUND

Body-mounted monitoring devices are worn on the skin of a user. In some embodiments, the monitoring devices are worn by the user for multiple days via an adhesive layer that couples to the monitoring device and the skin of the user. The adhesive layer may break down or start to fail over time. Thus, the monitoring device is removed from the user, the adhesive layer is removed from the monitoring device, a new adhesive layer is applied to the monitoring device, and the monitoring device is then reapplied to the skin of the user. Manual removal of the adhesive layer and subsequent alignment and application of the new adhesive layer is often difficult. It is also possible for the user to improperly orient the adhesive layer on the monitoring device. In some embodiments, the monitoring device is not worn continuously. In other embodiments, the monitoring device is worn continuously but is not operating continuously. In these instances, it is desirable to preserve the battery life of the monitoring device by selectively disabling the monitoring device.

DETAILED DESCRIPTION

Figure 1:
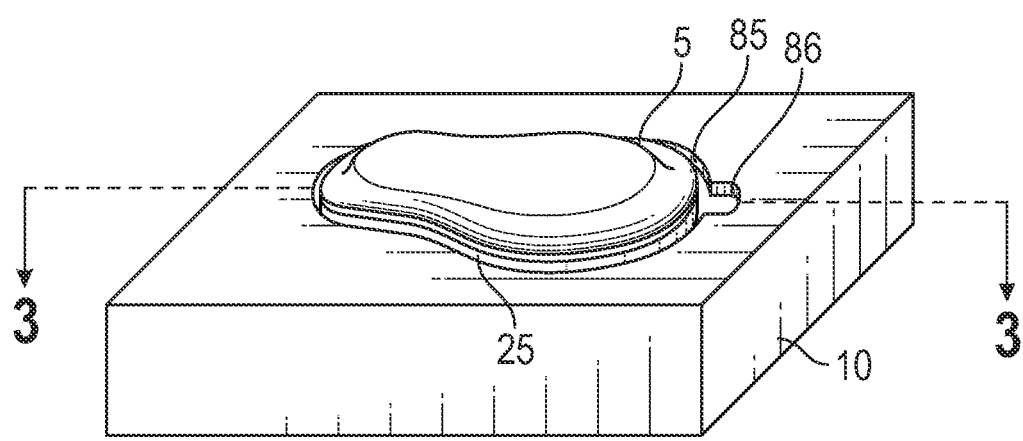
FIG. 1 is a diagrammatic illustration of a monitoring device and an adhesive applicator, according to an example embodiment.

The following disclosure provides many different embodiments or examples. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

Body-mounted monitoring devices are worn on the skin of a user. In some embodiments, the monitoring devices are worn by the user for multiple days via an adhesive layer that couples to the monitoring device and the skin of the user. The adhesive layer may break down or start to fail over time. Thus, the monitoring device is removed from the user, the adhesive layer is removed from the monitoring device, a new adhesive layer is applied to the monitoring device, and the monitoring device is then reapplied to the skin of the user. Manual removal of the adhesive layer and subsequent alignment and application of the new adhesive layer is often difficult. It is also possible that the user improperly orients the adhesive layer on the monitoring device. In some embodiments, the monitoring device is not worn continuously. In other embodiments, the monitoring device is worn continuously but is not operating continuously. In these instances, it is desirable to preserve the battery life of the monitoring device by selectively disabling the monitoring device.

A monitoring device is generally referred to by the reference numeral 5 and an adhesive applicator is generally referred to by the reference number 10 as illustrated in FIG. 1. As illustrated in FIG. 1, the monitoring device 5 is coupled to the adhesive applicator 10, which aligns and applies a new adhesive layer to the monitoring device 5.

Figure 2:
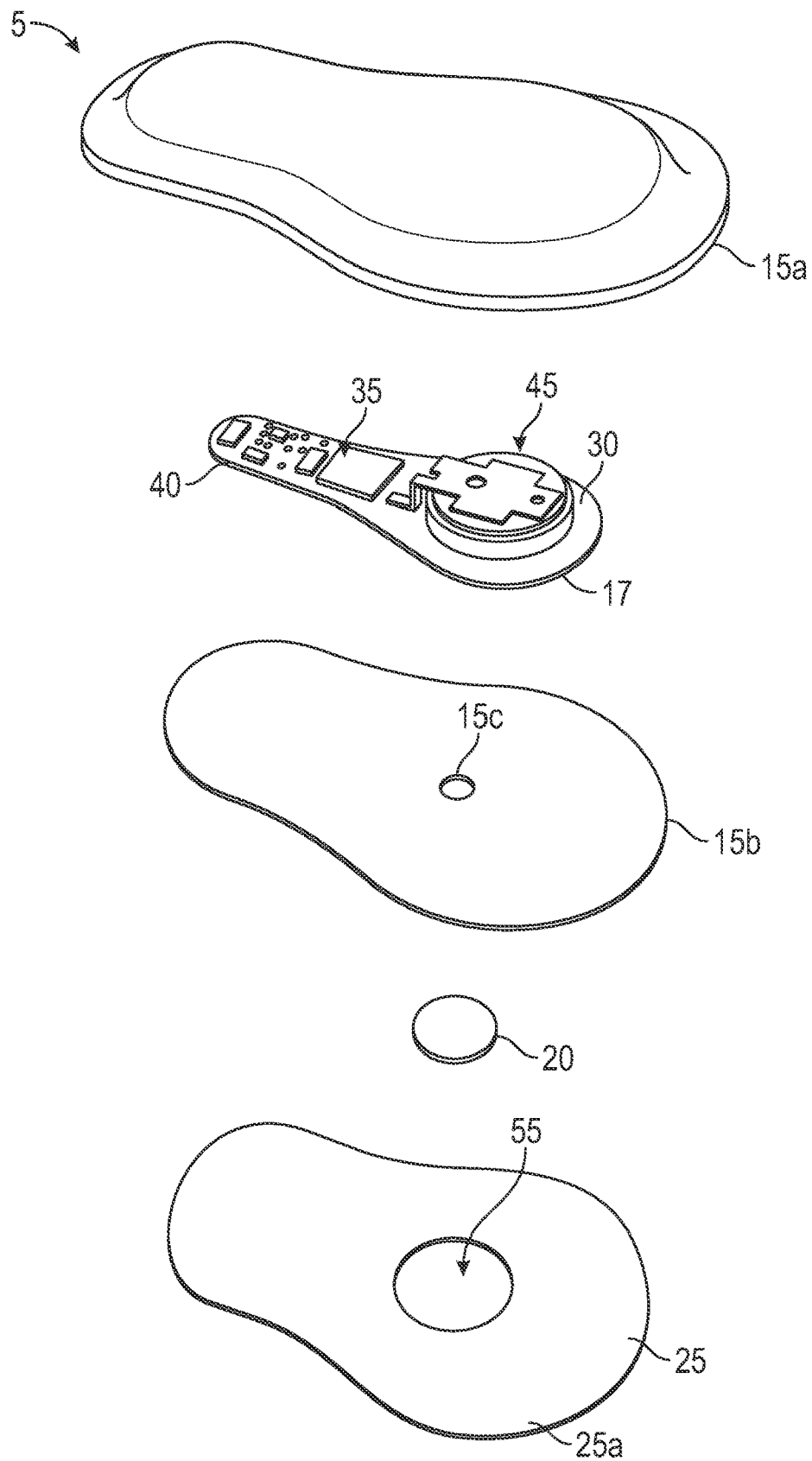
FIG. 2 is an exploded view of the monitoring device of FIG. 1, according to an example embodiment.
Figure 3:
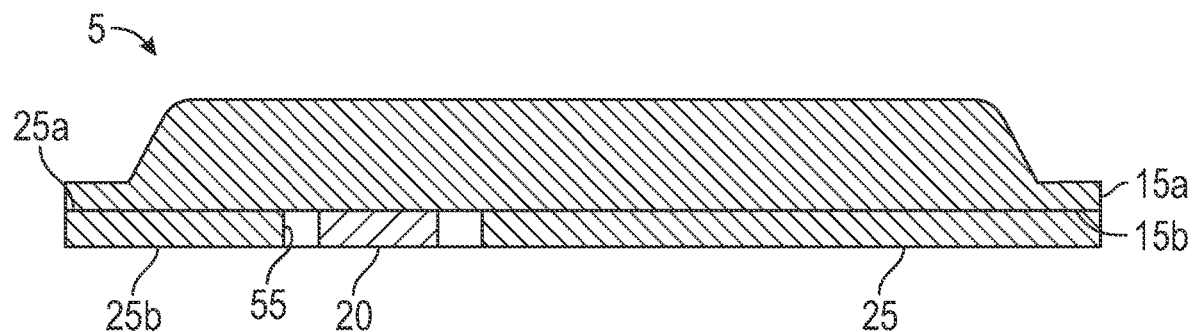
FIG. 3 is a sectional view of the monitoring device of FIG. 1, according to an example embodiment.

As illustrated in FIG. 2 and/or FIG. 3, the monitoring device 5 includes an upper housing 15a and a complimentary lower housing 15b that is configured to couple to the upper housing 15a. In some embodiments, the monitoring device 5 is reusable or configured to be removed and reattached to the patient multiple times. In some embodiments, the device 5 is a patch-like device that is attached, via adhesive or otherwise, to the torso of the patient. When the housings 15a and 15b are coupled together, a chamber is formed that houses a control system 17. A thermal contact 20 is coupled to the lower housing 15b and is in communication with the control system 17 via an opening 15c formed in the lower housing 15b. A double-sided adhesive layer 25 is in contact with the lower housing 15b.

In an example embodiment, the housings 15a and 15b are elastomeric housings.

In some embodiments, the control system 17 includes a substrate 30, a thermal sensor 35, a microcontroller 40, and a power supply 45. In some implementations, the substrate 30 can be a circuit board or printed circuit board (PCB). Additional or fewer components are possible. For example, the control system 17 may include an accelerometer, a humidity sensor, or other biometric sensors that are in communication with the microcontroller 40. The thermal sensor 35 is in communication with the microcontroller 40 and the thermal contact 20. Generally, the microcontroller 40 includes a processor and a memory. The microcontroller 40 is configured for wireless communication with a remote device via a network. In an example embodiment, the network includes the Internet, one or more local area networks, a bluetooth low energy network, one or more wide area networks, one or more cellular networks, one or more wireless networks, one or more voice networks, one or more data networks, one or more communication systems, and/or any combination thereof.

In some embodiments, an opening 55 is formed in the adhesive layer 25. In some embodiments, the opening 55 has a diameter that is greater than the outer diameter of the thermal contact 20. However, in other embodiments, the diameter of the opening 55 is equal to or less than the outer diameter of the thermal contact 20. In some examples, the thermal contact 20 facilitates physical measurement of properties of the body of the wearer (e.g., of the skin at the external body surface). As shown, the thermal contact 20 is a circular, rounded contact configured to protrude from the lower housing 15b and to make electrical and/or thermal contact with the skin of the external body surface of the wearer. In some embodiments, the thermal contact 20 extends between about 0.05 cm and about 0.2 cm from the lower housing 15b. In some embodiments, the contact 20 is in electrical contact with the thermal sensor 35 such that a galvanic skin response ("GSR") of the skin at the external body surface can be detected by the monitoring device 5. However, in other embodiments, the contact 20 is in thermal contact only with the thermal sensor 35. In some embodiments, the temperature sensor 35 is a thermal sensor, which may be a thermistor, a resistance temperature detector ("RTD"), a capacitance temperature sensor, a semiconductor device, or an infrared camera. Generally, the thermal contact 20 and the thermal sensor 35 are positioned and configured to continuously monitor and detect a temperature of the patient. In other embodiments, the thermal contact 20 and the thermal sensor 35 are positioned and configured to intermittently monitor the temperature of the patient. For example, the thermal contact 20 and the thermal sensor 35 may detect a temperature every 1 minute, every 30 seconds, every 5 seconds, every 1 second, or every 0.5 second. Regardless, the thermal contact 20 and the thermal sensor 35 monitor or detect a temperature of the patient. In some embodiments, the thermal contact 20 is a metal disc.

The adhesive layer 25 can be a double-sided adhesive layer having has one surface 25a that includes an adhesive configured to couple the adhesive layer 25 to the lower housing 15b and another opposing surface 25b that includes an adhesive configured to couple to the patient. In some embodiments, the adhesive on the surface 25a is different from the adhesive on the surface 25b. In some embodiments, the adhesive is selected to have material properties permitting it to be peeled from the patient's skin by pulling a corner or edge from the skin at an angle from the skin within a range from about 10 to 170 degrees without damaging the skin. In addition and in some embodiments, the adhesive can be removed without damaging the skin without the use of water, soap, solvent or other releasing material. In some embodiments, the adhesive is selected to have an adhesion to LDPE, 180 Degree peel of 15-50 oz/inch width, and more particularly, about 20-50 oz/inch width, and more particularly, about 30-40 oz/inch width, and even more particularly, about 35-37 oz/inch width. The adhesive may be a skin-friendly, rubber based adhesive. Further, the adhesive is configured so that in some embodiments, less than 10% of the adhesive remains on the skin as residue. In other embodiments, less than 5% of the adhesive remains on the skin as residue. In some embodiments, the adhesive layer 25 attaches the monitoring device 5 to the skin of the patient in a manner that also couples the thermal contact 20 to the skin of the patient.

In an example embodiment, the power source 45 is a battery or the like.

In some embodiments, the monitoring device 5 is configured to operate in a battery preservation mode. In some embodiments, the monitoring device 5 automatically enters battery preservation mode upon detection of a disabling event. However, in other embodiments, the user can instruct the monitoring device 5 to enter battery preservation mode. One example of the monitoring device 5 automatically entering the battery preservation mode upon detection of a disabling event includes the microcontroller 40 determining that the temperature detected by the thermal sensor 35 is below a minimum temperature. In some embodiments, the minimum temperature is a minimum temperature associated with the thermal sensor 35 being in contact with the skin of the user. Thus, the detected temperature being below the minimum temperature is an indication that the monitoring device 5 is not being coupled to the patient. When this occurs, the control system 17 transitions into a sleep or idle mode. In some embodiments, the monitoring device 5 includes an additional sensor, such as for example, a capacitive sensor, an accelerometer, and an audio sensor (or any combination thereof), with each being in communication with the microcontroller 40. For example, when the additional sensor is the capacitive sensor, the capacitive sensor is positioned to contact the skin of the user when the monitoring device 5 is coupled to the user. Upon determination, by the microcontroller 40 and based on the conditions detected by the capacitive sensor, that the capacitive sensor is no longer in contact with the user, the monitor 5 enters battery preservation mode (e.g. sleep or idle mode). However, when the additional sensor is the accelerometer and in some embodiments, the disabling event may be lack of movement (breathing movement) by the user over a period of time, thereby indicating that the monitoring device is not coupled to the user. In other embodiments and when the audio sensor is the additional sensor, the disabling event may be the absence of an audible heartbeat, or other audible marker emitted by the patient, that is detectable when the monitoring device is coupled to the user. The control system 17 may include a combination of sensors to improve the identification of a disabling event. In some instances, when in sleep or idle mode, the control system 17 periodically or intermittently reawakens or partially reawakens to determine if the temperature sensed by the thermal sensor 35 is equal to or greater than the minimum temperature. If so, then the control system 17 resumes normal operations. In other embodiments, and when the microcontroller 40 is wirelessly coupled to a second device via a mobile application and a network, the control system enters battery preservation mode upon receipt of an instruction from the second device via the mobile application and the network. In some embodiments, the remote device is a smart phone, tablet computer, personal digital assistant (PDA), or personal computing device (PCDs), or the like. In other embodiments, the user depresses or otherwise activates an on/off button that is in communication with the microcontroller 40. The input from the on/off button alternatively instructs the monitoring device 5 to enter and exit the battery preservation mode.

In an example embodiment, the monitoring device 5 entering the battery preservation mode preserves battery life. Thus, when the power supply 45 is a non-rechargeable battery, the ability to preserve battery life extends the design life of the monitoring device 5.

Figure 4:
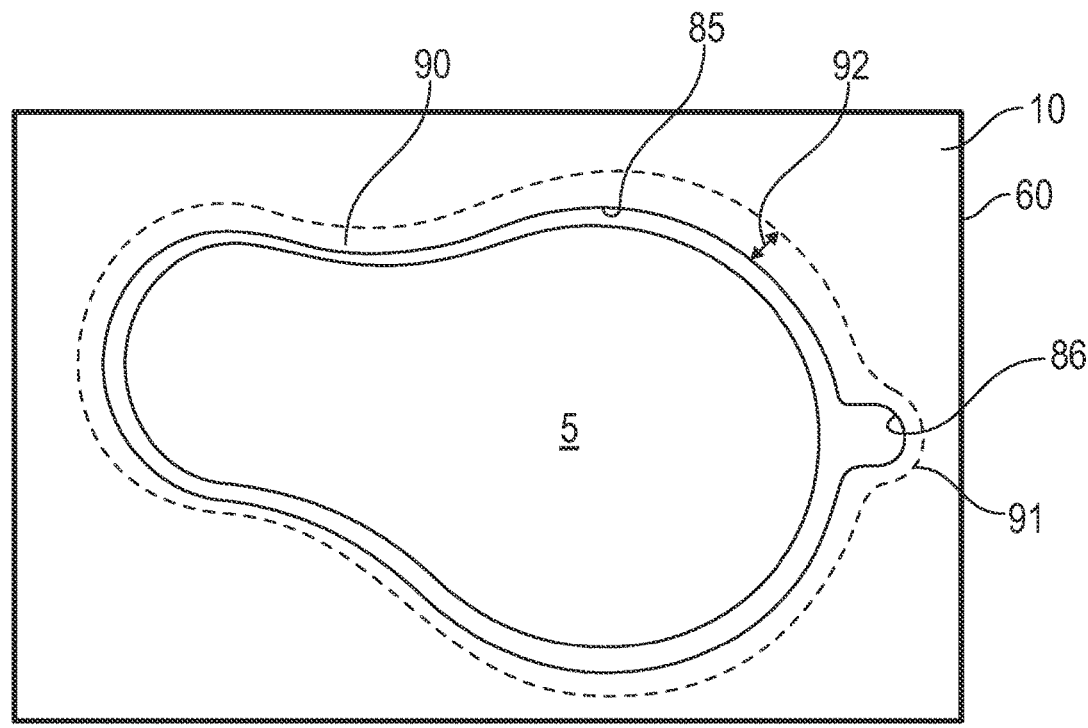
FIG. 4 is a top view of the monitoring device and the adhesive applicator of FIG. 1, according to an example embodiment.

In an example embodiment and in reference to FIGS. 1, 4, and/or 5 the adhesive applicator 10 includes a housing 60 that forms an internal chamber 65. A movable floor 70 moves relative to a floor 65a of the chamber 65. In some embodiments, one or more energized springs 75 are positioned between the movable floor 70 and the floor 65a of the chamber, to push the movable floor 70 in a direction 80a in FIG. 5. In some embodiments, an opening 85 is formed in the housing 60. The chamber 65 is accessible via the opening 85. As illustrated in FIG. 4, the opening 85 generally corresponds to the footprint of the monitoring device 5, or the lower housing 15b. In some embodiments, the opening 85 corresponds to the footprint of the monitoring device 5 except for a pull tab opening 86 that forms a portion of the opening 85. Generally, an internal shoulder 87 is formed in the housing 60 due to a size difference between the opening 85 and the chamber 65. In some embodiments, the footprint of the lower housing 15b is a shape that is non-symmetrical in at least one direction. Thus, there is only one alignment of the lower housing 15b to the opening 85 that results in the lower housing 15b being aligned and received in the opening 85. In an example embodiment, adhesive liners 90 and adhesive layers 25 are alternatively stacked on the floor 70. Generally, the adhesive liners 90 have a similar shaped footprint to the opening 85 except that the size of the liner 90 is larger than the size of the opening 85. A pull tab protrusion 91 forms a portion of the liner 90 and corresponds to the pull-tab opening 86. In some embodiments, the size difference between the liner 90 and the opening 85 results in an outer periphery 92 of the liner 90 extending under the shoulder 87 of the housing 60. In some embodiments, the adhesive liners 90 are positioned in the opening 85 such that the pull tab protrusion 91 of each adhesive liner 90 is positioned below the pull tab opening 86. The adhesive layers 25 are positioned relative to the opening 85 and on the floor 70 such that when the lower housing 15b is received within the opening 85, the adhesive layer 25 is correctly or properly aligned with the lower housing 15b. For example, the openings 55 of the adhesive layers 25 are aligned within the housing 60 such that each receive (consecutively) the thermal contact 20 when the monitoring device 5 is placed within the opening 85. In some embodiments, a conductive gel 95 or liquid that improves the coupling between the thermal contact and a user's skin is loaded or accommodated within the opening 55 of each adhesive layer 25. In some embodiments, a spacer or a glue dot 100 is positioned between each liner 90 at a position that is spaced from the adhesive layers 25. For example, the glue dot 100 is positioned between the pull tab protrusions 91 of the liners 90 and below the pull tab opening 86 of the housing 60. The glue dot 100 is sized or formed of a material that pushes or otherwise enables the pull tab protrusion 91 to move from a first position to a second position. When in the first position, the pull tab protrusion 91 is positioned between the shoulder 87 and the floor 65a (under the shoulder 87). When in the second position, the pull tab protrusion 91 extends through the openings 85 and 86 and over a top surface 60a of the housing 60 (over the shoulder 87).

In some embodiments, the liners 90 are composed of a material that prevents the adhesive layers 25 from sticking or adhering to the liners 90.

Figure 5:
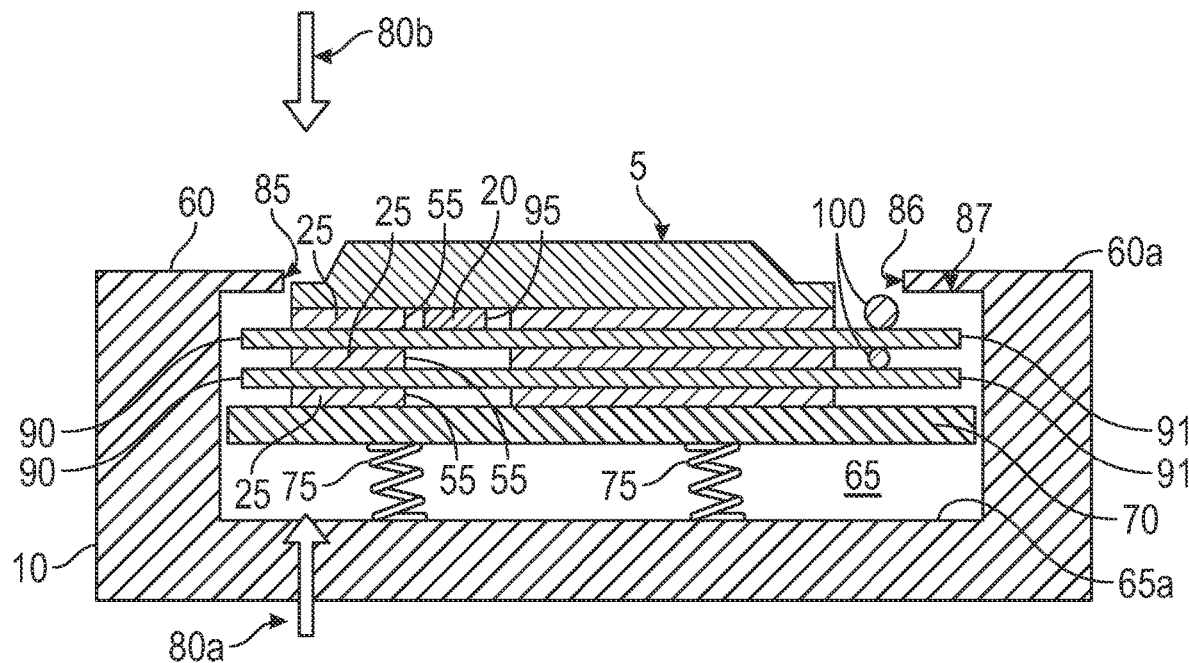
FIG. 5 is a cross-sectional view of the monitoring device and the adhesive applicator along the line 3-3 of FIG. 1, according to an example embodiment.

The device 5 and/or the applicator 10 can be altered in a variety of ways. For example, the springs 75 may be omitted and replaced with a variety of force generating elements. For example, the springs 75 may be replaced with Belleville washers, resilient arms, resilient buttons, air bag, etc. As illustrated in FIG. 5, to apply the adhesive layer 25, the device 5 is moved in direction 80b, which is perpendicular to the bottom surface of the bottom housing 15b. However, in other embodiments, the opening 85 may be configured such that the device 5 enters the chamber 65 in a direction parallel to the bottom surface of the bottom housing 15b. In this embodiment, the height of the monitor 5 is designed such that the shape of the monitor 5 is non-symmetrical in at least one direction and there is only one proper alignment of the device 5 relative to the housing 60 to allow the device 5 to enter the opening 85. In some embodiments, use of the applicator 10 is not limited to the device 5. Instead, the applicator 10 is configured to apply adhesive layers to any adhesive-based wearable device. Moreover, and in some embodiments, the applicator 10 may include a pusher and/or cap such that the device 5 is forced in the direction 80b via the pusher and/or cap independently from a (manual) force applied by the user in the direction 80b.

Figure 6:
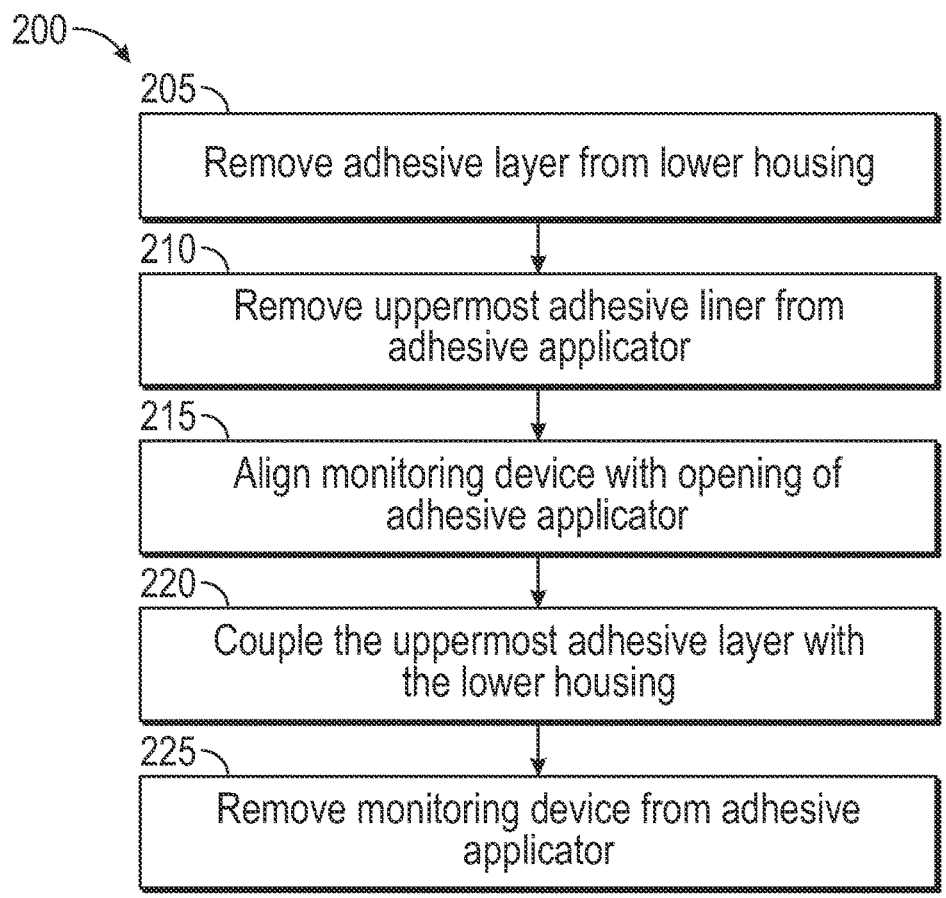
FIG. 6 is a flow chart illustrating a method of operating the system of FIGS. 1-5, according to an example embodiment.

FIG. 6 is a flow chart illustrating a method 200 of operating the device 5 and the applicator 10 of FIGS. 1-5, according to an example embodiment. Generally, the method 200 includes removing the adhesive layer 25 from the lower housing 15b at step 205, removing an uppermost adhesive liner 90 from the adhesive applicator 10 at step 210, aligning the monitoring device 5 with the opening 85 of the adhesive applicator 10 at step 215, coupling the uppermost adhesive layer 25 with the lower housing 15b at step 220, and removing the monitoring device 5 from the adhesive applicator at step 225.

At the step 205, the adhesive layer 25 is removed from the lower housing 15b of the monitoring device 5. In some example embodiments, removing the adhesive layer 25 is performed manually. That is, a user peels the adhesive layer 25 off of the lower housing 15b.

Figure 7:
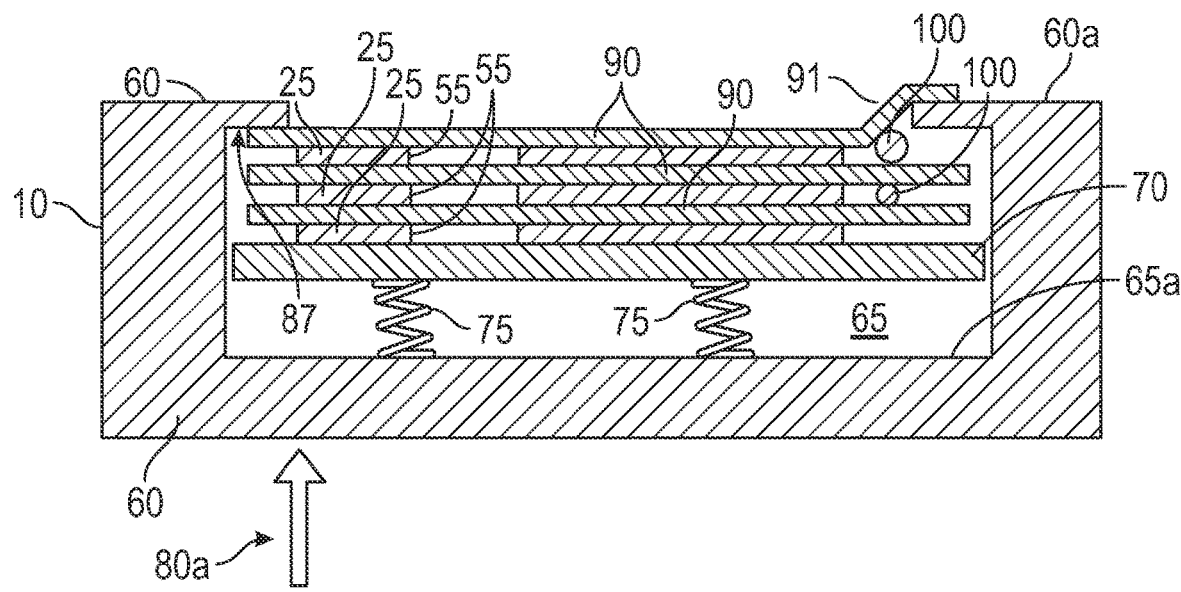
FIG. 7 is a cross-sectional view of the monitoring device during a step of the method of FIG. 6, according to an example embodiment.

At the step 210, the uppermost adhesive liner 90 is removed from the adhesive applicator 10. For example and as illustrated in FIG. 7, the adhesive applicator 10 is illustrated in a first configuration in which the uppermost adhesive liner 90 remains coupled to the adjacent adhesive layer 25, thereby protecting the adhesive layer 25 from the environment external to the housing 60. As illustrated, the glue dot 100 has encouraged the pull tab protrusion 91 into the second position. That is, the pull tab protrusion extends through the openings 85 and 86 and is visible and accessible to a user of the applicator 10. During the step 210, the user grips the pull tab protrusion 91 and pulls the protrusion 91 and thus the liner 90, away from the glue dot 100 and the adjacent adhesive layer 25 to place the adhesive applicator 10 in a second configuration. In the second configuration and in some embodiments, as the periphery 92 of the liner 90 is no longer in contact with the shoulder 87 of the housing 60 due to the liner 90 being removed. Thus, the floor 70 moves in the direction 80a until the periphery 92 of the uppermost liner 90 contacts the shoulder 87. Thus, and in some embodiments, the shoulder 87 is a stop against the floor 70 movement in the direction 80a. In some embodiments and when the adhesive applicator is in the second configuration, a portion of the adhesive layer 25 extends within the opening 85.

At the step 215, the monitoring device 5 is aligned with the opening 85 of the applicator 10. Due to shape of the monitoring device 5 and the corresponding opening 85, there is generally only one alignment of the device 5 and the opening 85 that allows the monitoring device 5 to enter into the opening 85. Aligning the monitoring device 5 in the opening 85 also automatically aligns the thermal contact 20 into the opening 55 of the uppermost adhesive layer 25.

At the step 220, the uppermost adhesive layer 25 is coupled to the lower housing 15b. In some embodiments, and as illustrated in FIG. 5, the user moves the monitoring device 5 into the opening 85 in the direction 80b until the springs 75 are fully compressed, to couple the surface 25a of the adhesive layer 25 to the lower surface of the lower housing 15b.

At the step 225, the monitoring device 5 is removed from the applicator 10. During the step 225, the monitoring device 5, including the uppermost adhesive layer 25, is lifted from the applicator 10 to expose another uppermost adhesive liner 90.

Generally, the steps 205-225 are repeated as desired to remove a used adhesive layer and apply a new adhesive layer to the monitoring device.

In some embodiments, the step 205 is omitted and the new adhesive layer 25 is applied over an old adhesive layer 25 that remains on the device 5.

Figure 8:
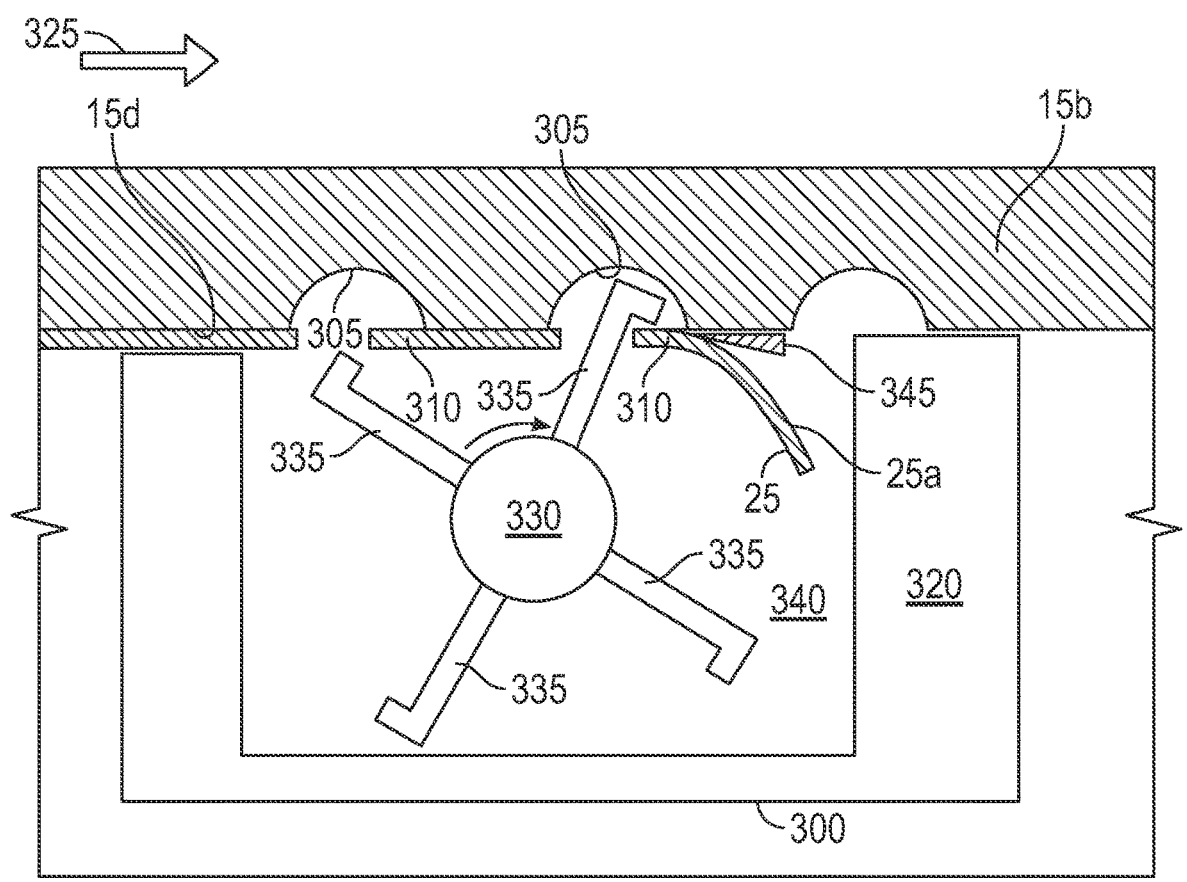
FIG. 8 is a sectional view of a portion of the monitoring device and a portion of an adhesive layer removal device, according to an example embodiment.

In some embodiments and during the step 205, the adhesive layer 25 is removed using an adhesive layer removal device 300. As illustrated in FIG. 8, a bottom portion of the housing 15b forms recessed pockets 305 that extend away from a surface 15d on which the adhesive layer 25 is adhered. In some embodiments, portions of the adhesive layer 25 include stiffeners 310 or portions that are more rigid than other portions of the adhesive layer 25. In some embodiments, the adhesive layer 25 forms openings 315 that correspond with the pockets 305. In some embodiments, the removal device 300 includes a support 320 on which the device 5 moves relative to in a direction 325. A rotating device 330 having arms 335 extending therefrom is accommodated in a chamber 340 of the device 330. In some embodiments, the device 300 also includes a wedge 345 adjacent the rotating device 330. In some embodiments, the arms 335 are sized and configured to extend through the openings 315 and into the pockets 305. When the device 5, including the adhesive layer 25, is supported on the support 320 and moved in the direction 325, the arms 335 extend through the openings 315 and into the pockets 305. In some embodiments, some of the stiffeners 310 of the adhesive layer 25 extend over a portion of the pockets 305. In some embodiments, the arms 335 contact the stiffeners 310, and rotation of the rotating device 330 continues, the arms 335 pull the stiffeners 310 and the adhesive layer 25 away from the housing 10b. In some embodiments, the wedge 345 encourages the removal of the layer 25 from the housing 10b and directs the removed portion of the layer 25 into the chamber 340. While the rotating device 330 is shown having arms having hooked end portions that hook onto the stiffeners 310 of the layer 25, any type of removal elements can be used to pull the adhesive layer 25 from the housing 10b. In some embodiments, the removal device 300 applies a liquid solution during the step 205 to encourage separation of the layer 25 from the housing 10b.

In some embodiments, the device 5 moves relative to the device 300 in a direction that is opposite the direction 325. In some embodiments, the removal device 300 forms a portion of the adhesive applicator 10.

In some embodiments, use of the monitoring device 5 and the adhesive applicator 10 and/or the method 200 results in the adhesive layers 25 being properly applied to the monitor 5, thereby preventing misalignment of the layer 25 and the monitor 5, which reduces the reliability of the adhesion between the monitor 5 and the user. Misalignment of the adhesive layer 25 and the monitor 5 also increases the likelihood that debris can enter between the device 5 and the user, which reduces the reliability of the measurements and operation of the monitor 5. Generally, body-mountable sensing devices, such as the device 5, being disposable is desirable for user convenience. However, body-mountable sensing devices typically have high fixed cost due to the cost of the electronic components, required assembly, etc. Use life is typically not limited by the electronic capability or the power supply 45 (e.g., battery), but instead by the life of the adhesive layer 25. In some embodiments, providing the device 5 and method of using the device 5 together with the ability of the device 5 to enter into battery preservation mode, increases the number of uses of the device 5. This reduces the cost per use of the device 5 while avoiding significant burden to the user. The applicator 10 ensures that the surface 25a is coupled to the bottom of the housing 10b and the surface 25b of the layer 25 is exposed and available to be coupled to the skin of the patient. Moreover, the monitoring device 5 is configured to enter into a battery preservation mode between uses to extend the life of the power supply 45 (e.g., battery). In an example embodiment, the monitoring device 5 is a non-rechargeable monitor and is not intended to be recharged. Moreover, the ability to re-apply the adhesive layers 25 to the monitor 5 allows for better defined battery life, a potential to use a gentler adhesive, and re-application of the adhesive layer 25 in cases of mis-application. In some embodiments, the applicator 10 forms a portion of the packaging of the monitoring device 5.

Generally, any creation, storage, processing, and/or exchange of user data associated the method, apparatus, and/or system disclosed herein is configured to comply with a variety of privacy settings and security protocols and prevailing data regulations, consistent with treating confidentiality and integrity of user data as an important matter. For example, the apparatus and/or the system may include a module that implements information security controls to comply with a number of standards and/or other agreements. In some embodiments, the module receives a privacy setting selection from the user and implements controls to comply with the selected privacy setting. In other embodiments, the module identifies data that is considered sensitive, encrypts data according to any appropriate and well-known method in the art, replaces sensitive data with codes to pseudonymize the data, and otherwise ensures compliance with selected privacy settings and data security requirements and regulations.

Figure 9:
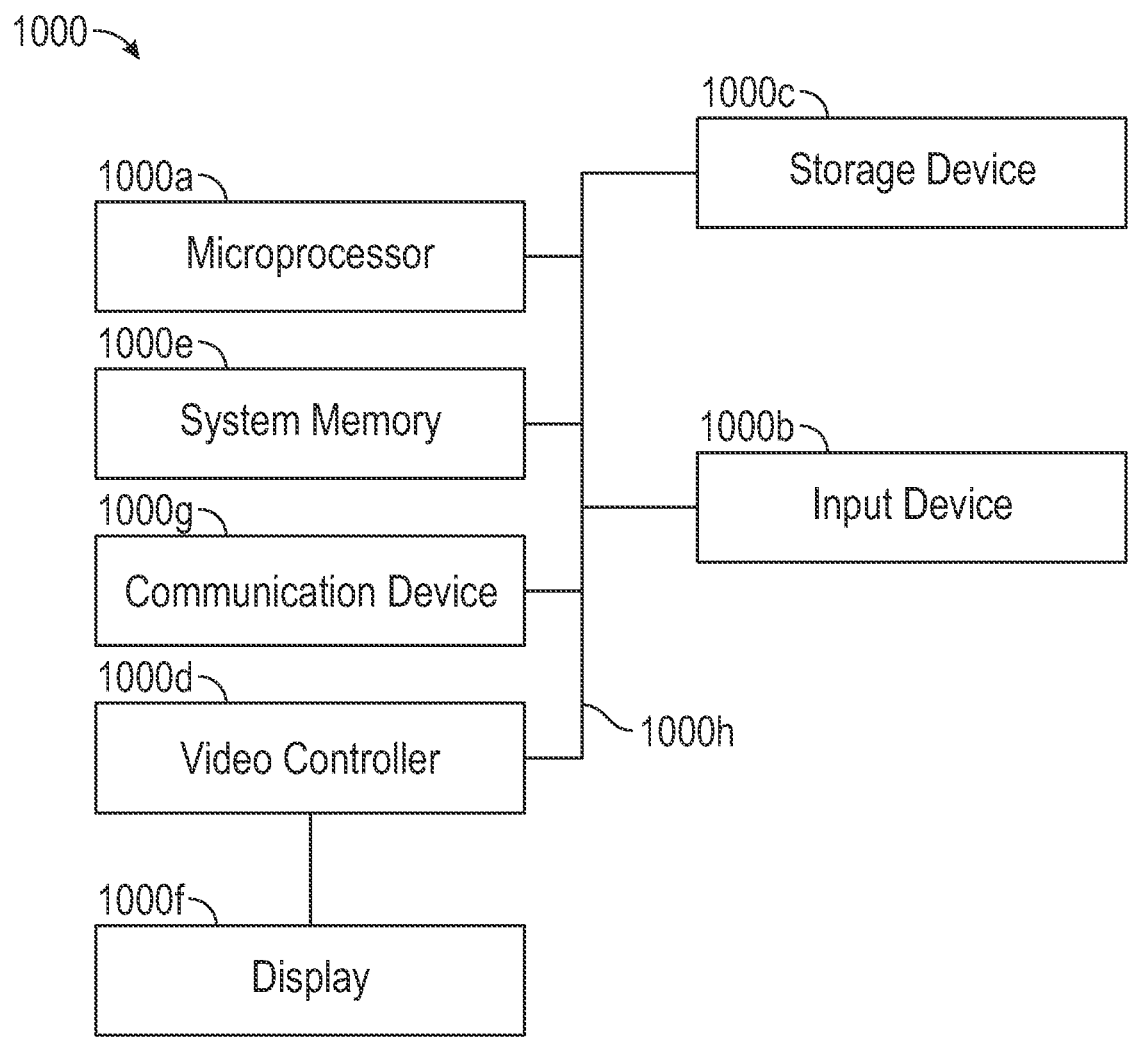
FIG. 9 is a diagrammatic illustration of a node for implementing one or more example embodiments of the present disclosure, according to an example embodiment.

In an example embodiment, as illustrated in FIG. 9 with continuing reference to FIGS. 1-8, an illustrative node 1000 for implementing one or more of the example embodiments described above and/or illustrated in FIGS. 1-8 is depicted. The node 1000 includes a microprocessor 1000a, an input device 1000b, a storage device 1000c, a video controller 1000d, a system memory 1000e, a display 1000f, and a communication device 1000g all interconnected by one or more buses 1000h. In several example embodiments, the storage device 1000c may include a hard drive, CD-ROM, optical drive, any other form of storage device and/or any combination thereof. In several example embodiments, the storage device 1000c may include, and/or be capable of receiving, a CD-ROM, DVD-ROM, or any other form of computer-readable medium that may contain executable instructions. In several example embodiments, the communication device 1000g may include a modem, network card, or any other device to enable the node to communicate with other nodes. In several example embodiments, any node represents a plurality of interconnected (whether by intranet or Internet) computer systems, including without limitation, personal computers, mainframes, PDAs, smartphones and cell phones.

In several example embodiments, one or more of the components of the systems described above and/or illustrated in FIGS. 1-8, include at least the node 1000 and/or components thereof, and/or one or more nodes that are substantially similar to the node 1000 and/or components thereof. In several example embodiments, one or more of the above-described components of the node 1000, the monitoring device 5 and/or the adhesive applicator 10 include respective pluralities of same components.

In several example embodiments, one or more of the applications, systems, and application programs described above and/or illustrated in FIGS. 1-8, include a computer program that includes a plurality of instructions, data, and/or any combination thereof; an application written in, for example, Arena, HyperText Markup Language (HTML), Cascading Style Sheets (CSS), JavaScript, Extensible Markup Language (XML), asynchronous JavaScript and XML (Ajax), and/or any combination thereof; a web-based application written in, for example, Java or Adobe Flex, which in several example embodiments pulls real-time information from one or more servers, automatically refreshing with latest information at a predetermined time increment; or any combination thereof.

In several example embodiments, a computer system typically includes at least hardware capable of executing machine readable instructions, as well as the software for executing acts (typically machine-readable instructions) that produce a desired result. In several example embodiments, a computer system may include hybrids of hardware and software, as well as computer sub-systems.

In several example embodiments, hardware generally includes at least processor-capable platforms, such as client-machines (also known as personal computers or servers), and hand-held processing devices (such as smart phones, tablet computers, personal digital assistants (PDAs), or personal computing devices (PCDs), for example). In several example embodiments, hardware may include any physical device that is capable of storing machine-readable instructions, such as memory or other data storage devices. In several example embodiments, other forms of hardware include hardware sub-systems, including transfer devices such as modems, modem cards, ports, and port cards, for example.

In several example embodiments, software includes any machine code stored in any memory medium, such as RAM or ROM, and machine code stored on other devices (such as flash memory, or a CD ROM, for example). In several example embodiments, software may include source or object code. In several example embodiments, software encompasses any set of instructions capable of being executed on a node such as, for example, on a client machine or server.

In several example embodiments, combinations of software and hardware could also be used for providing enhanced functionality and performance for certain embodiments of the present disclosure. In an example embodiment, software functions may be directly manufactured into a silicon chip. Accordingly, it should be understood that combinations of hardware and software are also included within the definition of a computer system and are thus envisioned by the present disclosure as possible equivalent structures and equivalent methods.

In several example embodiments, computer readable mediums include, for example, passive data storage, such as a random access memory (RAM) as well as semi-permanent data storage such as a compact disk read only memory (CD-ROM). One or more example embodiments of the present disclosure may be embodied in the RAM of a computer to transform a standard computer into a new specific computing machine. In several example embodiments, data structures are defined organizations of data that may enable an embodiment of the present disclosure. In an example embodiment, a data structure may provide an organization of data, or an organization of executable code.

In several example embodiments, any networks and/or one or more portions thereof may be designed to work on any specific architecture. In an example embodiment, one or more portions of any networks may be executed on a single computer, local area networks, client-server networks, wide area networks, internets, hand-held and other portable and wireless devices and networks.

In several example embodiments, a database may be any standard or proprietary database software. In several example embodiments, the database may have fields, records, data, and other database elements that may be associated through database specific software. In several example embodiments, data may be mapped. In several example embodiments, mapping is the process of associating one data entry with another data entry. In an example embodiment, the data contained in the location of a character file can be mapped to a field in a second table. In several example embodiments, the physical location of the database is not limiting, and the database may be distributed. In an example embodiment, the database may exist remotely from the server, and run on a separate platform. In an example embodiment, the database may be accessible across the Internet. In several example embodiments, more than one database may be implemented.

In several example embodiments, a plurality of instructions stored on a non-transitory computer readable medium may be executed by one or more processors to cause the one or more processors to carry out or implement in whole or in part the above-described operation of each of the above-described example embodiments of the system, the method, and/or any combination thereof. In several example embodiments, such a processor may include one or more of the microprocessor 1000*a*, any processor(s) that are part of the components of the system, and/or any combination thereof, and such a computer readable medium may be distributed among one or more components of the system. In several example embodiments, such a processor may execute the plurality of instructions in connection with a virtual computer system. In several example embodiments, such a plurality of instructions may communicate directly with the one or more processors, and/or may interact with one or more operating systems, middleware, firmware, other applications, and/or any combination thereof, to cause the one or more processors to execute the instructions.

A method is disclosed that includes aligning a lower housing of a monitoring device with an opening of an adhesive applicator; positioning the lower housing of the monitoring device within the opening to couple an uppermost adhesive layer that is positioned within the adhesive applicator with the lower housing; and removing the monitoring device from the opening of the adhesive applicator. In one embodiment, a shape of the lower housing of the monitoring device corresponds to a shape of the opening of the adhesive applicator; and wherein aligning the monitoring device with the opening of the adhesive applicator includes matching the orientation of the lower housing to the orientation of the opening of the adhesive applicator. In one embodiment, the adhesive applicator includes: a housing forming an internal chamber and the opening through which the internal chamber is accessible; a spring-loaded floor that moves between a floor of the internal chamber and the opening; wherein the uppermost adhesive layer is one of a plurality of adhesive layers; wherein the plurality of adhesive layers and a plurality of adhesive liners are alternatively stacked on the spring-loaded floor; wherein a top surface of the uppermost adhesive layer is coupled to a first adhesive liner of the plurality of adhesive liners and a bottom surface of the uppermost adhesive layer is coupled to a second adhesive liner of the plurality of adhesive liners; and wherein the method further includes removing the first adhesive liner to expose the top surface of the uppermost adhesive layer before coupling the uppermost adhesive layer with the lower housing. In one embodiment, the opening is defined by an internal shoulder formed in the housing; wherein the second adhesive liner has a size that is greater than the size of the opening; and wherein the method further includes the spring-loaded floor pushing the second adhesive liner against the internal shoulder formed in the housing such that a periphery of the second adhesive liner contacts the internal shoulder. In one embodiment, pushing the second adhesive liner against the internal shoulder formed in the housing results in the uppermost adhesive layer extending within the opening. In one embodiment, the second adhesive liner includes a pull tab; and wherein, when the second adhesive liner is pushed against the internal shoulder formed in the housing, the pull tab extends outside of the housing. In one embodiment, a spacer is positioned between the first and second adhesive liners; and wherein the spacer encourages the pull tab to extend outside of the housing. In one embodiment, the lower housing of the monitoring device forms a plurality of recessed pockets; wherein the uppermost adhesive layer forms a plurality of openings; wherein a portion of the uppermost adhesive layer extends over a portion of the recessed pockets when the uppermost adhesive layer is adhered to the lower housing; wherein the method further includes removing the uppermost adhesive layer from the lower housing of the monitoring device; and wherein removing the uppermost adhesive layer from the lower housing includes moving the monitoring device relative to a plurality of rotating arms such that the arms extend within at least a portion of the plurality of openings and the recessed pockets and pull the uppermost adhesive layer from the lower housing. In one embodiment, the method also includes the monitoring device entering a battery preservation mode upon detecting that the monitoring device is not coupled to a skin of a user. In one embodiment, the method also includes the monitoring device entering a battery preservation mode upon receiving an instruction, from a user, to enter battery preservation mode.

An adhesive layer applicator for a body-mountable device is disclosed that includes a housing defining an opening through which a chamber is accessible; and a plurality of adhesive layers and a plurality of adhesive liners alternatively stacked on a floor that is movable within the chamber; wherein the size and shape of the opening corresponds to the size and shape of the body-mountable device; and wherein the opening is configured to receive at least a portion of the body-mountable device. In one embodiment, the floor is spring-loaded; and wherein the floor is movable between a floor of the chamber and the opening. In one embodiment, the plurality of adhesive layers and the plurality of adhesive liners are positioned within the housing such that when the body-mountable device is received in the opening, one of the plurality of adhesive layers contacts the body-mountable device. In one embodiment, the shape of the body-mountable device is not-symmetrical in at least one direction. In one embodiment, a footprint of the plurality of adhesive layers is smaller than a footprint of the plurality of adhesive liners; and wherein a spacer is positioned between two consecutive adhesive liners and offset from each of the adhesive layers.

An apparatus is disclosed that includes a body-mountable device that includes an upper housing coupled to a lower housing; and an adhesive applicator including: a housing forming an internal chamber and a first opening through which the chamber is accessible; a spring-loaded floor that moves between a floor of the chamber and the first opening; and a plurality of adhesive layers and a plurality of adhesive liners alternatively stacked on the spring-loaded floor; wherein the size and shape of the first opening corresponds to the size and shape of the lower housing of the body-mountable device; and wherein the first opening is configured to receive the lower housing of the body-mountable device. In one embodiment, the body-mountable device further includes a thermal contact extending from the lower housing; wherein a second opening is formed in an uppermost adhesive layer in the plurality of adhesive layers; and wherein the thermal contact aligns with and extends within the second opening of the uppermost adhesive layer when the first opening receives the lower housing of the body-mountable device. In one embodiment, a conductive gel is accommodated within the second opening. In one embodiment, the shape of the lower housing is not-symmetrical in at least one direction; and wherein the shape of the first opening is not-symmetrical in at least one direction. In one embodiment, each layer in the plurality of adhesive layers includes an adhesive configured to be applied to a skin of a patient; and wherein each adhesive liner in the plurality of adhesive liners includes a pull tab that is sized to remove the adhesive liner from an adjacent adhesive layer.

It is understood that variations may be made in the foregoing without departing from the scope of the present disclosure.

In several example embodiments, the elements and teachings of the various illustrative example embodiments may be combined in whole or in part in some or all of the illustrative example embodiments. In addition, one or more of the elements and teachings of the various illustrative example embodiments may be omitted, at least in part, and/or combined, at least in part, with one or more of the other elements and teachings of the various illustrative embodiments.

Any spatial references such as, for example, "upper," "lower," "above," "below," "between," "bottom," "vertical," "horizontal," "angular," "upwards," "downwards," "side-to-side," "left-to-right," "right-to-left," "top-to-bottom," "bottom-to-top," "top," "bottom," "bottom-up," "top-down," etc., are for the purpose of illustration only and do not limit the specific orientation or location of the structure described above.

In several example embodiments, while different steps, processes, and procedures are described as appearing as distinct acts, one or more of the steps, one or more of the processes, and/or one or more of the procedures may also be performed in different orders, simultaneously and/or sequentially. In several example embodiments, the steps, processes and/or procedures may be merged into one or more steps, processes and/or procedures.

In several example embodiments, one or more of the operational steps in each embodiment may be omitted. Moreover, in some instances, some features of the present disclosure may be employed without a corresponding use of the other features. Moreover, one or more of the above-described embodiments and/or variations may be combined in whole or in part with any one or more of the other above-described embodiments and/or variations.

Although several example embodiments have been described in detail above, the embodiments described are example only and are not limiting, and those skilled in the art will readily appreciate that many other modifications, changes and/or substitutions are possible in the example embodiments without materially departing from the novel teachings and advantages of the present disclosure. Accordingly, all such modifications, changes and/or substitutions are intended to be included within the scope of this disclosure as defined in the following claims. In the claims, any means-plus-function clauses are intended to cover the structures described herein as performing the recited function and not only structural equivalents, but also equivalent structures. Moreover, it is the express intention of the applicant not to invoke 35 U.S.C. § 112, paragraph 6 for any limitations of any of the claims herein, except for those in which the claim expressly uses the word "means" together with an associated function.

What we claim is:

1. An adhesive layer applicator for a body-mountable device, the applicator comprising:
   a housing defining a first opening through which a chamber is accessible; and
   a plurality of adhesive layers and a plurality of adhesive liners alternately stacked on a floor that is movable within the chamber;
   wherein the size and shape of the first opening corresponds to the size and shape of the body-mountable device;
   wherein the housing is configured to receive at least a portion of the body-mountable device through the first opening;
   wherein a second opening is formed in each adhesive layer in the plurality of adhesive layers; and
   wherein a gel is accommodated within the second openings.

2. The applicator of claim 1, wherein the gel is conductive.

3. The applicator of claim 1,
   wherein the floor is spring-loaded; and
   wherein the floor is movable between a floor of the chamber and the first opening.

4. The applicator of claim 3, wherein the plurality of adhesive layers and the plurality of adhesive liners are positioned within the housing such that when the body-mountable device is received in the first opening, one of the plurality of adhesive layers contacts the body-mountable device.

5. The applicator of claim 3, wherein the shape of the body-mountable device is not-symmetrical in at least one direction.

6. The applicator of claim 1, wherein a footprint of the plurality of adhesive layers is smaller than a footprint of the plurality of adhesive liners.

7. The applicator of claim 6,
   wherein the first opening is defined by an internal shoulder formed in the housing; and
   wherein the footprint of the plurality of adhesive layers being smaller than the footprint of the plurality of adhesive liners results in an outer periphery of the liners extending under the shoulder.

8. The applicator of claim 7, wherein each adhesive liner in the plurality of adhesive liners comprises a pull tab that is sized to remove the adhesive liner from an adjacent adhesive layer.

9. The applicator of claim 8, wherein, when the plurality of adhesive layers and the plurality of adhesive liners are pushed against the internal shoulder formed in the housing, one of the pull tabs extends outside of the housing.

10. The applicator of claim 1, wherein a spacer is positioned between two consecutive adhesive liners and offset from each of the adhesive layers.

11. The applicator of claim 1,
    wherein the body-mountable device comprises:
       a lower housing; and
       a thermal contact extending from the lower housing; and
    wherein each of the second openings has a diameter that is greater than an outer diameter of the thermal contact.

12. The applicator of claim 1, wherein each layer in the plurality of adhesive layers comprises an adhesive configured to be applied to a skin of a patient.

13. An adhesive layer applicator for a body-mountable device, the applicator comprising:
    a housing forming an internal chamber and a first opening through which the internal chamber is accessible;
    a spring-loaded floor that moves between a floor of the chamber and the first opening; and
    a plurality of adhesive layers and a plurality of adhesive liners alternately stacked on the spring-loaded floor;
    wherein the first opening is configured to receive a portion of the body-mountable device;
    wherein a second opening is formed in each adhesive layer in the plurality of adhesive layers; and
    wherein a conductive gel is accommodated within the second openings.

14. The applicator of claim 13,
    wherein the body-mountable device comprises:
       a lower housing; and
       a thermal contact extending from the lower housing; and
    wherein each of the second openings has a diameter that is greater than an outer diameter of the thermal contact.

15. The applicator of claim 13, wherein the plurality of adhesive layers and the plurality of adhesive liners are positioned within the housing such that when at least a portion of the body-mountable device is received in the opening, one of the plurality of adhesive layers contacts the body-mountable device.

16. The applicator of claim 13, wherein a footprint of the plurality of adhesive layers is smaller than a footprint of the plurality of adhesive liners.

17. The applicator of claim 16,
    wherein the first opening is defined by an internal shoulder formed in the housing; and
    wherein the footprint of the plurality of adhesive layers being smaller than the footprint of the plurality of adhesive liners results in an outer periphery of the liners extending under the shoulder.

18. The applicator of claim 13, wherein each adhesive liner in the plurality of adhesive liners comprises a pull tab that is sized to remove the adhesive liner from an adjacent adhesive layer.

* * * * *